United States Patent
Metz (10) Patent No.: US 10,722,394 B2
(45) Date of Patent: Jul. 28, 2020

(54) DENTAL ORTHOTIC STRUT HAVING MULTIPLE AXES OF MOVEMENT

(71) Applicant: James Metz, Columbus, OH (US)

(72) Inventor: James Metz, Columbus, OH (US)

( * ) Notice: Subject to any disclaimer, the term of this patent is extended or adjusted under 35 U.S.C. 154(b) by 1220 days.

(21) Appl. No.: 14/449,493

(22) Filed: Aug. 1, 2014

(65) Prior Publication Data

US 2014/0349243 A1 Nov. 27, 2014

Related U.S. Application Data

(63) Continuation-in-part of application No. 13/239,498, filed on Sep. 22, 2011, now Pat. No. 8,875,713.

(51) Int. Cl.
*A61F 5/56* (2006.01)
*A61C 7/36* (2006.01)

(52) U.S. Cl.
CPC .............. *A61F 5/566* (2013.01); *A61C 7/36* (2013.01)

(58) Field of Classification Search
CPC ..... A61C 7/36; A61C 7/08; A61F 5/56; A61F 5/566; A61F 2005/563; A61F 2/3099; A61F 2002/30991
USPC ........................................................ 433/19
See application file for complete search history.

(56) References Cited

U.S. PATENT DOCUMENTS

| | | | |
|---|---|---|---|
| 5,378,147 A * | 1/1995 | Mihailowitsch | A61C 7/36 433/18 |
| 6,012,920 A | 1/2000 | Woo | |
| 6,832,911 B2 * | 12/2004 | Forster | A61C 7/36 433/19 |
| 7,178,529 B2 | 2/2007 | Kownacki | |
| 7,448,388 B2 | 11/2008 | Halstrom | |
| 7,578,671 B2 * | 8/2009 | Corcoran | A61C 7/36 433/179 |
| 7,637,262 B2 | 12/2009 | Bailey | |
| 7,987,854 B2 | 8/2011 | Arni | |
| 2007/0224567 A1 | 9/2007 | Robson | |
| 2009/0007817 A1 | 1/2009 | Branjnovic | |

(Continued)

FOREIGN PATENT DOCUMENTS

| | | |
|---|---|---|
| DE | 10 2007 039 761 A1 * | 9/2009 |
| WO | WO 2014/130870 A1 * | 8/2014 |

OTHER PUBLICATIONS

International Search Report and Written Opinion of the International Searching Authority for International Application No. PCT/US2012/055705, dated Nov. 23, 2012. 8 pages.

(Continued)

*Primary Examiner* — Anna K Kinsaul
*Assistant Examiner* — Camtu T Nguyen
(74) *Attorney, Agent, or Firm* — Michael J. Gallagher (57) ABSTRACT

A dental orthotic strut having at least one multi-axis rotable joint connecting the strut to either a maxillary and/or mandibular retainer attached to the teeth. Jaw advancement may be accomplished by periodically replacing the strut with a new strut having a slightly longer minimum length, thereby advancing the resting position of the closed jaw. The rotable joint or joints allow greater freedom of movement and comfort when the jaw is opened in a non-sagittal plane. A plurality of strut pairs having a same length, but with progressively longer sets of strut pairs is generally supplied, so that left and right struts can be progressively replaced with longer struts over time.

17 Claims, 8 Drawing Sheets

(56) References Cited

U.S. PATENT DOCUMENTS

| | | | | |
|---|---|---|---|---|
| 2010/0311003 | A1* | 12/2010 | Kozlov | A61F 5/566 433/2 |
| 2013/0177861 | A1* | 7/2013 | Hayes | A61C 7/36 433/19 |
| 2014/0057222 | A1* | 2/2014 | Kumar | A61C 7/36 433/19 |
| 2014/0255866 | A1* | 9/2014 | Faust | A61C 7/36 433/19 |
| 2015/0289956 | A1* | 10/2015 | Nameta | A61C 8/005 29/896.1 |

OTHER PUBLICATIONS

Kato, Thie, Huynh, Miyawaki, and Lavigne, "Topical Review: Sleep Bruxism and the Role of Peripheral Sensory Influences," Journal of Orofacial Pain 2003; 191-213.

Van Lunteren and Dick, "Motor Unit Regulation of Mammalian Pharyngeal Dilator Muscle Activity," Journal of Clinical Investigation vol. 84, Aug. 1989, 577-585.

Tsuiki, Ryan, Lowe, Inoue, "Functional contribution of mandibular advancement to awake upper airway patency in obstructive sleep apnea," Sleep Breath 2007; 11: 245-251.

Rossetti, Araujo, Rossetti and Conti, "Association Between Rhythmic Masticatory Muscle Activity During Sleep and Masticatory Myofascial Pain: A Polysomnographic Study," Journal of Orofacial Pain vol. 22, No. 3, 2008, 190-200.

Huynh, Rompre, Montplaisir, Manzini, Okura and Lavigne, "Comparison of Various Treatments for Sleep Bruxism Using Determinants of Number Needed to Treat and Effect Size," The International Journal of Prosthodontics vol. 19, No. 5, 2006, 435-441.

Johal, Gill, Ferman and McLaughlin, "The effect of mandibular advancement appliances on awake upper airway and masticatory muscle activity in patients with obstructive sleep apnoea," Clinical Physiology and Functional Imaging (2007) 27, pp. 47-53.

* cited by examiner

DENTAL ORTHOTIC STRUT HAVING MULTIPLE AXES OF MOVEMENT

CROSS-REFERENCE TO RELATED APPLICATIONS

This application is a Continuation-in-Part of U.S. patent application Ser. No. 13/239,498, filed Sep. 22, 2011; the specification of which is disclosed as if fully rewritten herein.

STATEMENT REGARDING FEDERALLY SPONSORED RESEARCH OR DEVELOPMENT

Not applicable.

TECHNICAL FIELD

The present disclosure relates generally to the field of dental orthotics, including a means for the advancement of the lower jaw, relative to the upper, and in particular, to both rigid and resilient dental orthotics having struts capable of multiple axes of movement.

BACKGROUND OF THE INVENTION

A large number of persons have varying degrees of upper airway obstruction presenting with varied degrees of symptoms. As the upper airway begins with the nose and mouth, it is not surprising that the nose, tongue, and jaw all make contributions to such obstructive syndromes.

Various treatment modalities have been suggested. Various airway pressure devices, such as continuous positive airway pressure devices (CPAP) have been successfully used, although these tend to be both cumbersome and uncomfortable. More recently, dental orthotics have been employed. One general class of orthotic relies upon shifting the position of the lower jaw, generally moving the jaw forward, to displace the tongue anteriorly and thereby help clear the upper airway. Obviously, it is difficult to shift the jaw anteriorly without an external anchor point, so these orthotic have also presented problems of utility and comfort.

A classical means for advancement of the jaw is the Herbst appliance. The Herbst appliance is a fixed, tooth-borne, functional orthodontic appliance in which jaw position is influenced by a pin-and-tube spring-loaded appliance that is cemented or bonded to the teeth.

In particular, the Herbst appliance, or Herbst-type orthotics, often suffer from a number of practical problems. Generally, these devices are semi-permanently bonded to the teeth, and while they can be removed by a practitioner, they are not generally amenable to removal by the wearer. These appliances generally utilize spring-loaded struts, in order that a continuous pressure may be applied to advance the jaw.

Another class of orthotic, and in particular that described by Robson (U.S. Pat. No. 5,752,822) relies on positioning the tongue on an extension that elevates the tongue and causes the tongue to move forward to an upward position resting on the extension. These devices are designed to manipulate the airway by changing the position of the tongue.

SUMMARY OF THE INVENTION

In its most general configuration, the presently disclosed dental orthotic advances the state of the art with a variety of new capabilities and overcomes many of the shortcomings of prior devices and methods in new and novel ways. In its most general sense, the presently disclosed dental orthotic overcomes the shortcomings and limitations of the prior art in any of a number of generally effective configurations.

The dental orthotics described herein generally, in at least one embodiment, have at least a maxillary retainer for cooperating with and reversibly attaching to a plurality of maxillary teeth, a mandibular retainer for cooperating with and reversibly attaching to a plurality of mandibular teeth, and a variable-length rigid strut connecting the retainers.

The strut may have an internal strut length adjuster at least partially enclosed within the strut body and the internal strut length adjuster is adjustable to change the adjustable length when the orthotic is in a wearing position. This alone is a significant advantage over the prior art, most if not all of which require removal from a patient's mouth before strut length can be adjusted.

In an embodiment, the maxillary retainer and the mandibular retainer may be releasably and elastically joined by an elastic closure that facilitates a passive closure of the jaw. In various embodiments, the device may have jaw displacement indicia on the maxillary retainer and the mandibular retainer. As a relative anterior-posterior relationship between the maxillary retainer and the mandibular retainer changes, the position of the indicia relative to each proportionally changes, allowing a practitioner to make fine and measured adjustments in jaw displacement. The visual indicia allows relative jaw displacement to be easily seen, and thus recorded, helping provide metric guide points in the treatment of various disorders through jaw advancement.

In some embodiments, the device may have at least one maxillary fenestration, and the mandibular retainer may have at least one mandibular fenestration. These fenestrations, in at least one effect, provide for greater wearer comfort by allowing more space for tongue movement.

In another embodiment, the dental orthotic comprises at least one resilient strut attached to a maxillary retainer and a mandibular retainer. The resilient strut uses the resilience of its component material to effect a slight advancement of the jaw by placing the strut a distance slightly less than the strut length between the maxillary and mandibular retainers This shortened distance, relative to the strut length, causes a lateral deviation in the strut, which by its resilient intrinsic nature therefore applies a forward force in attempting to straighten itself.

As described previously, embodiments may include an elastic closure to promote jaw closure, and may also have at least one maxillary fenestration and/or at least one mandibular fenestration.

In such resilient strut embodiments, at least one embodiment may include jaw displacement indicia including visually perceptible resilient strut length indicia. However, these do not serve to make small mechanical adjustments to strut length, as seen with the adjustable length strut, but rather to quickly and visually indicate a relative anterior-posterior relationship between the maxillary retainer and the mandibular retainer. In the case of the resilient strut embodiments, this is to immediately and accurately identify a predetermined combination of strut length and relative jaw displacement.

In another series of embodiments, an orthotic may include at least a maxillary retainer for cooperating with and reversibly attaching to a plurality of maxillary teeth, a mandibular retainer for cooperating with and reversibly attaching to a plurality of mandibular teeth, and a rigid strut having a fixed minimum length but that is extensile beyond such fixed minimal length, connecting the retainers. Jaw advancement may be accomplished by periodically replacing the strut with new struts (struts being generally employed as a pair of struts having a left and a right pair member), having a slightly greater fixed minimum length. This fixed minimal length can create a tensile force when compressed and thereby provide a force on the jaw, when at rest, tending to advance the jaw, similar to the method in which a more obviously resilient strut also exerts a force.

Additionally, the fixed minimum-length strut of the present invention may have at least one multi-axis rotable joint connecting the strut to either/or the maxillary and/or mandibular retainer, allowing a degree of non-sagittal opening and closing of the jaw.

Embodiments may comprise a method and system for jaw advancement utilizing a plurality of resilient struts of progressively longer length, or struts having a fixed minimum-length. The steps of the method may include: Molding a plurality of maxillary retainers and mandibular retainers, affixing a strut of a first length to the retainers to provide slight jaw advancement, and then observing it in use in a patient, as described above. As the jaw is advanced over time, progressively longer struts may be employed on the retainers to continue the advancement. While it would be possible to practice the method with only replacing the struts and keeping the same retainers in use, it has been found practical to mold a plurality of retainers, and then to employ new retainers with each change of strut length.

The assessment of a final desired jaw advancement may be made by a number of methods, which may include but are not limited to; subjective sense of airway improvement by the wearer, a measurement of a resting heart rate at an ambient atmosphere of the wearer, the achievement of an advancement to a predetermined amount of advancement by objective metrics, measuring and comparing resting arterial blood oxygen saturation level at an ambient atmosphere of the wearer to predetermined levels, and/or measuring and comparing a resting heart rate at an ambient atmosphere of the wearer to predetermined levels.

Numerous variations, modifications, alternatives, and alterations of the various preferred embodiments, processes, and methods may be used alone or in combination with one another as will become more readily apparent to those with skill in the art with reference to the following detailed description of the preferred embodiments and the accompanying figures and drawings.

BRIEF DESCRIPTION OF THE DRAWINGS

Without limiting the scope of the dental orthotic strut as disclosed herein and referring now to the drawings and figures.

These drawings are provided to assist in the understanding of the exemplary embodiments of the dental orthotic strut as described in more detail below and should not be construed as unduly limiting a dental orthotic or the dental orthotic strut. In particular, the relative spacing, positioning, sizing and dimensions of the various elements illustrated in the drawings are not drawn to scale and may have been exaggerated, reduced or otherwise modified for the purpose of improved clarity. Those of ordinary skill in the art will also appreciate that a range of alternative configurations have been omitted simply to improve the clarity and reduce the number of drawings.

DETAILED DESCRIPTION OF THE INVENTION

The disclosed anti-obstructive airway dental orthotic enables a significant advance in the state of the art. The preferred embodiments of the dental orthotic accomplish this by new and novel arrangements of elements and methods that are configured in unique and novel ways and which demonstrate previously unavailable but preferred and desirable capabilities. The description set forth below in connection with the drawings is intended merely as a description of the presently preferred embodiments of the dental orthotic, and is not intended to represent the only form in which the dental orthotic may be constructed or utilized. The description sets forth the designs, functions, means, and methods of implementing the dental orthotic in connection with the illustrated embodiments. It is to be understood, however, that the same or equivalent functions and features may be accomplished by different embodiments that are also intended to be encompassed within the spirit and scope of the claimed dental orthotic.

In a first series of embodiments, described in detail and illustrated in U.S. patent application Ser. No. 13/239,498, filed Sep. 22, 2011; the specification of which is disclosed as if fully rewritten herein, an anti-obstructive airway dental orthotic is reversibly attached to the teeth, obviating many of the problems associated with fixed appliances. As described throughout this specification the terms anterior and posterior shall describe relative positions to each other, and shall mean as follows: Anterior shall mean more distant from a coronal, or frontal plane, relative to the term posterior, which shall mean closer to a coronal, or frontal plane. Additionally, the term practitioner shall mean any person practicing the invention, which may be, by way of example and not limitation, any one of a wide variety of health care practitioners.

In one component, there may be a maxillary retainer for cooperating with and reversibly attaching to a plurality of maxillary teeth, and the maxillary retainer includes a maxilla to strut attachment. In another component, there may be a mandibular retainer for cooperating with and reversibly attaching to a plurality of mandibular teeth, and the mandibular retainer includes a mandible to strut attachment.

Connecting the maxillary retainer and mandibular retainer, there may be a variable-length rigid strut including a strut body having an adjustable length. The strut may have an anterior end having a strut to mandible attachment, and a posterior end having a strut to maxilla attachment. The strut body has an internal strut length adjuster at least partially enclosed within the strut body and the internal strut length adjuster is adjustable to change the adjustable length when the orthotic is in a wearing position.

The maxilla to strut attachment cooperates with the strut to maxilla attachment to rotably and reversibly connect the maxillary retainer and the strut, and the mandible to strut attachment cooperates with the strut to mandible attachment to rotably and reversibly connect the mandible retainer and the strut.

In one embodiment, the maxilla to strut attachment may include a metal reinforced maxillary reinforcement, and the mandible to strut attachment may also include a metal reinforced mandibular reinforcement. Similarly, in some embodiments, the maxilla to strut attachment comprises an aramid fiber reinforced maxillary strut attachment and the mandible to strut attachment may comprise an aramid fiber reinforced maxillary reinforcement. Embodiments having a combination of metal and aramid reinforcement are particularly envisioned.

In an embodiment, the maxillary retainer may have a maxillary closure attachment and the mandibular retainer may have a mandibular closure attachment with an elastic closure reversibly connecting the maxillary closure attachment and mandibular closure attachment. This facilitates a passive closure of the jaw.

The dental orthotic may have jaw displacement indicia on the maxillary retainer and the mandibular retainer that cooperate to indicate a relative anterior-posterior relationship between the maxillary retainer and the mandibular retainer. This allows the practitioner to see the relative positions of the retainers and allows very small and precise adjustments to be easily seen and measured.

In some embodiments of the dental orthotic, the maxillary retainer may have at least one maxillary fenestration, and the mandibular retainer may have at least one mandibular fenestration. Embodiments in which both the maxillary retainer and the mandibular retainer have at least one fenestration are particularly envisioned. These fenestrations, in at least one effect, provide for greater wearer comfort by allowing more space for tongue movement.

In another embodiment, the dental orthotic comprises at least one resilient strut. There may be an anti-obstructive airway dental orthotic with at least one resilient strut having a strut body, at least a first at-rest length, an anterior end, and a posterior end. This may in turn cooperate in the maxillary region with a maxillary retainer cooperating with and reversibly attaching to a plurality of maxillary teeth and which has a fixed strut-maxilla attachment. Similarly, the dental retainer may have a mandibular retainer cooperating with and reversibly attaching to a plurality of mandibular teeth and having a fixed strut-mandible attachment.

The anterior end of the at least one resilient strut may be fixedly attached to the fixed strut-mandible attachment at a fixed strut-mandible attachment point and the posterior end of the at least one resilient strut may be fixedly attached to the fixed strut-maxilla attachment at a fixed strut-maxilla attachment point.

As described previously, an embodiment may incorporate a maxillary retainer having a maxillary closure attachment and a mandibular retainer having a mandibular closure attachment with an elastic closure reversibly connecting the maxillary closure attachment and mandibular closure attachment. Again, this helps facilitate a passive closure of the jaw.

Also as described previously, at least one embodiment may include jaw displacement indicia wherein the resilient strut includes visually perceptible resilient strut length indicia that indicate a relative anterior-posterior relationship between the maxillary retainer and the mandibular retainer. In the case of the resilient strut embodiments, this is to immediately and accurately identify a predetermined combination of strut length and relative jaw displacement.

In embodiments including a resilient strut, the dental orthotic may include a maxillary retainer having at least one maxillary fenestration or a mandibular retainer having at least one mandibular fenestration, or some combination of both. As detailed previously, these fenestrations may allow for greater wearer comfort. As would be known by one skilled in the art, the at least one resilient strut may include two resilient struts symmetrically disposed about a midline of the dental orthotic.

Embodiments may comprise a system for jaw advancement in which the resilient strut may include at least a resilient strut having a first at-rest length and at least a resilient strut having a second at-rest length.

Such a system may be invoked, by means of example and not limitation only, by steps that may include: Molding a plurality of maxillary retainers comprising at least a first maxillary retainer and a second maxillary retainer, to cooperate with a plurality of maxillary teeth fixed within a maxilla of a human wearer. Similarly, a practitioner may mold a plurality of mandibular retainers comprising at least a first mandibular retainer and a second mandibular retainer to cooperate with a plurality of mandibular teeth fixed within a mandible of the human wearer.

In a later step, the system may comprise attaching a posterior end of at least one resilient strut having a first at-rest length, at a fixed strut-maxilla attachment point on the first maxillary retainer. Subsequently, a practitioner may attach an anterior end of the at least one resilient strut having a first at-rest length, at a fixed strut-mandible attachment point on the first mandibular retainer. In such an arrangement, the fixed strut-maxilla attachment is relatively posterior to the fixed strut-mandible attachment point and a first straight line distance between the fixed strut-maxilla attachment point and the fixed strut-mandible attachment point is less than the first at-rest length. Thus it can be seen that different resilient strut lengths may produce differing degrees of relative jaw displacement when in use.

The system may be implemented including at least some of the following steps: a practitioner may releasably attach the first maxillary retainer to the plurality of maxillary teeth of the human wearer and releasably attach the first mandibular retainer to the plurality of mandibular teeth of the wearer and observe a period of time of attachment of the first maxillary retainer and the first mandibular retainer as joined by the resilient strut separating the retainers by a first straight line distance.

One skilled in the art will realize that this effects an advancement in an anterior-posterior direction of the mandible relative to the maxilla of the human wearer and the creation of a resultant second straight line distance between the fixed strut-maxilla attachment point and the fixed strut-mandible attachment point that is greater than the first straight line distance. When the practitioner is satisfied with the degree of advancement, the practitioner may remove the first maxillary retainer, the first mandibular retainer, and the at least one resilient strut from the human wearer.

Subsequently, the practitioner may attach a posterior end of at least one resilient strut having a second at-rest length, at a fixed strut-maxilla attachment point on the second maxillary retainer, and attach an anterior end strut to a fixed strut-mandible attachment point on the second mandibular retainer. The first straight line distance between the fixed strut-maxilla attachment point and the fixed strut-mandible attachment point is less than the second at-rest length, thereby allowing the resilient strut to exert an elastic pressure favoring jaw advancement.

As described earlier, the practitioner may then releasably attach the second maxillary retainer to the plurality of maxillary teeth of the human wearer and releasably attach the second mandibular retainer to the plurality of mandibular teeth of the wearer. By observing a period of time of attachment of the maxillary retainer and the mandibular retainer; an advancement in an anterior-posterior direction of the mandible relative to the maxilla of the human wearer is effected. This results in the creation of a resultant third straight line distance between the fixed strut-maxilla attachment point and the fixed strut-mandible attachment point that is greater than the second straight line distance.

Again, the practitioner may observe a period of time of attachment of the second maxillary retainer and the second mandibular retainer; and by repeating at least the steps above, gradually over time produce a final desired advancement in an anterior-posterior direction of the mandible relative to the maxilla of the human wearer.

One skilled in the art will know that the assessment of a final desired jaw advancement may be made with a number of methods, which may include but are not limited to; subjective sense of airway improvement by the wearer, a measurement of a resting heart rate at an ambient atmosphere of the wearer, the achievement of an advancement to a predetermined amount of advancement by objective metrics, measuring and comparing resting arterial blood oxygen saturation level at an ambient atmosphere of the wearer to predetermined levels, and/or measuring and comparing a resting heart rate at an ambient atmosphere of the wearer to predetermined levels.

In a further series of embodiments, seen well in FIGS. 1-8; in multiple embodiments, the disclosed invention provides for a dental orthotic strut having multiple axes of movement. One skilled in the art will realize that a traditional dental orthotic strut, such as that found in the well-known Herbst appliance, among others, is typically joined to the maxillary and mandibular portions of an orthotic with simple rotary joints, and is only capable of extension and contraction along a long axis of the strut. Since the human jaw rarely opens and closes in an entirely sagittal motion, this causes lateral and medial stresses to be produced on the orthotic, including any struts. Such lateral and medial stresses may displace the orthotic, contribute to wear and failure of the rotable joints, and contribute to significant patient discomfort. Therefore, a dental orthotic have multiple axes of movement, while maintaining the jaw-advancing qualities of traditional orthotic devices and their struts, is a considerable improvement.

In one embodiment, seen well in FIGS. 1-8, a dental orthotic strut (10) may have a posterior barrel (115), an anterior barrel (300), and a piston (200) connecting the two. As seen in FIGS. 1-5, the posterior barrel (100) may have a posterior barrel rearward end (102) having a posterior barrel anchor (115), a posterior barrel forward end (104), a posterior barrel exterior surface (110), and a posterior barrel external diameter (140).

The piston (200), seen well in FIGS. 1-4 and 8, may have a piston overall length (202), a piston retainer portion (210) having a piston retainer length (212), and a piston retainer diameter (214). There may be a piston working body portion (220) having a piston working body length (222) and a piston working body diameter (224), as well as a piston stem portion (230) having a piston stem length (232) and a piston stem diameter (234).

The anterior barrel (300), seen well in FIGS. 1-4 and 6, may have an anterior barrel rearward end (302) and an anterior barrel forward end (304) having an anterior barrel anchor (315), and an anterior barrel exterior surface (310). There may be an anterior barrel lumen (330) within the anterior barrel (300) having an anterior barrel lumen interior surface (320), an anterior barrel lumen first diameter (332), an anterior barrel lumen second diameter (333), and an anterior barrel rearward fenestration (336).

When the two barrels and piston are assembled, as seen in FIGS. 1-4, the piston stem portion (230) and piston working body portion (220) pass through the anterior barrel rearward fenestration (336), with the piston retainer diameter (214) being greater than the anterior barrel lumen second diameter (333) and less than the anterior barrel lumen first diameter (332). This movably retains the piston (200) within the anterior barrel lumen (330) and prevents the overall length of the piston (202) from fully passing through the anterior barrel rearward fenestration (336). The piston stem portion (230) may be fixed to the posterior barrel forward end (104). The piston stem portion (230) may be affixed to the posterior barrel (100) in a rigid joint, and such a rigid joint might include a welded joint, an adhered joint, and/or a press-fit joint.

One skilled in the art will realize several immediate advantages of the construction detailed above. First, the rotable retention of the piston (200) within the anterior barrel (300) allows for a rotable connection between the posterior barrel (100) and the anterior barrel (300), thereby allowing for non-sagittal opening and closing of the jaw. In some embodiments, a removable anchor pin (117), seen in FIG. 7, rotably attaches the posterior barrel anchor (115) to a mandibular portion of a dental orthotic and a removable anchor pin (117) rotably attaches the anterior barrel anchor (315) to the maxillary portion of the dental orthotic. Such a removable pin (117) system allows for a changing of struts (10) among multiple mandibular and maxillary portions. In other embodiments, the posterior barrel external diameter (140) is approximately equal to the anterior barrel external diameter (340), although this is not required. In other embodiments, the anterior barrel anchor (315) may be angulated at about a ten degree angle from a longitudinal axis of the anterior barrel (300), as seen well in FIGS. 2 and 3, for superior fit and comfort.

Second, while the length of the anterior barrel (300) may be fixed, the overall length of the strut may vary according to the length of the posterior barrel (100). Therefore, a lower jaw-advancing orthotic may be constructing by a providing an orthotic having removable and replaceable maxillary and mandibular portions which can be joined by removable and replaceable struts (10) having differing posterior barrel (100) lengths, all without compromising the multiple axes of movement of the strut (10). In an alternative embodiment, the maxillary and mandibular portions may be fixed to the teeth, as one familiar with the traditional construction of the Herbst appliance would know. In practice, having a posterior barrel (100) with an overall length of between 7.5 millimeters and 12.5 millimeters, as measured along a longitudinal axis of the posterior barrel (100) from a center of the posterior barrel anchor (115) to the posterior barrel forward end (104), has been found to be effective. In some embodiments, a plurality of pairs of struts (10), having 0.5 millimeter increments in length among the pairs, is employed.

Figure 1:
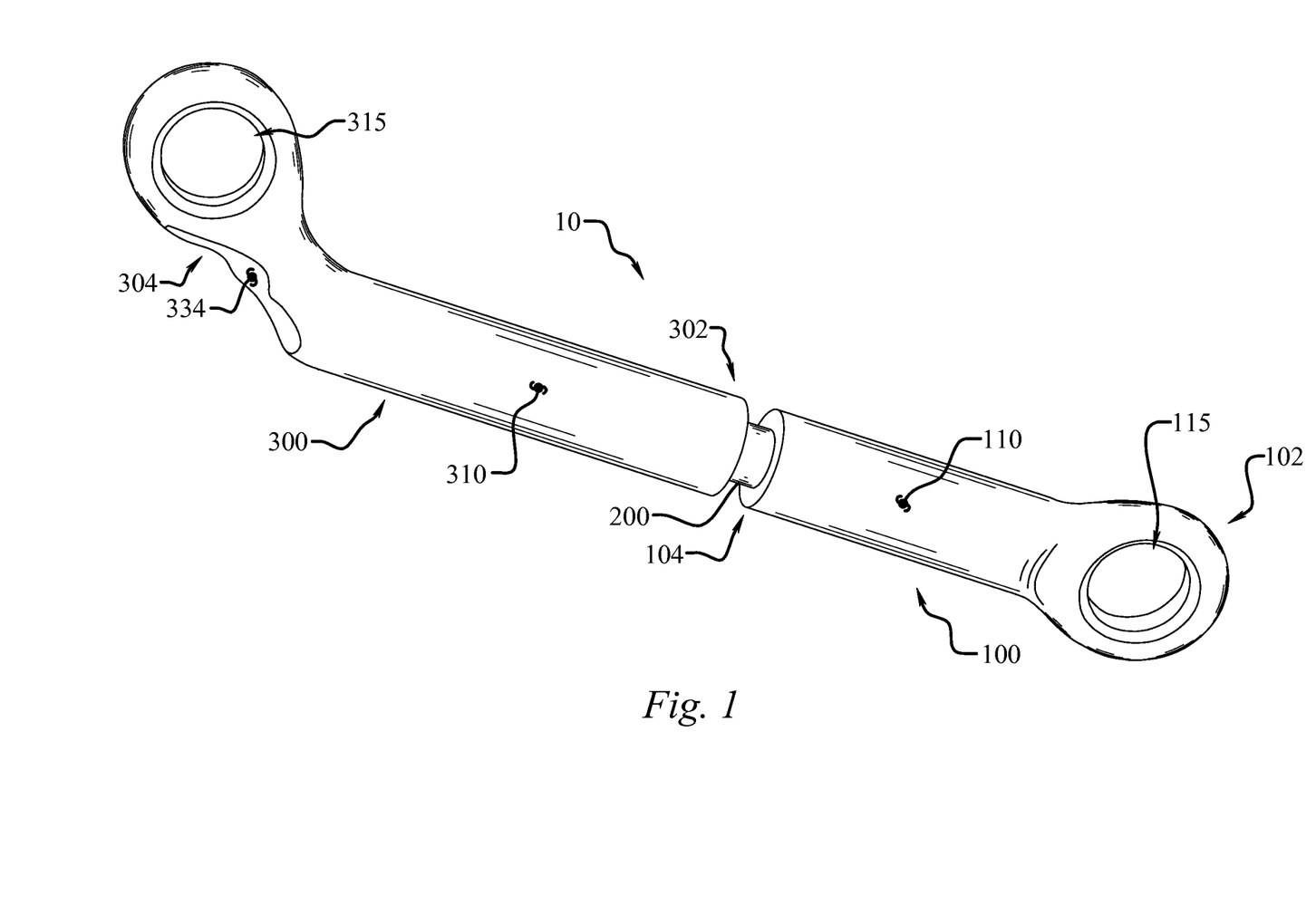
FIG. 1 is a side perspective view f a dental orthotic strut having multiple axes of movement.
Figure 2:
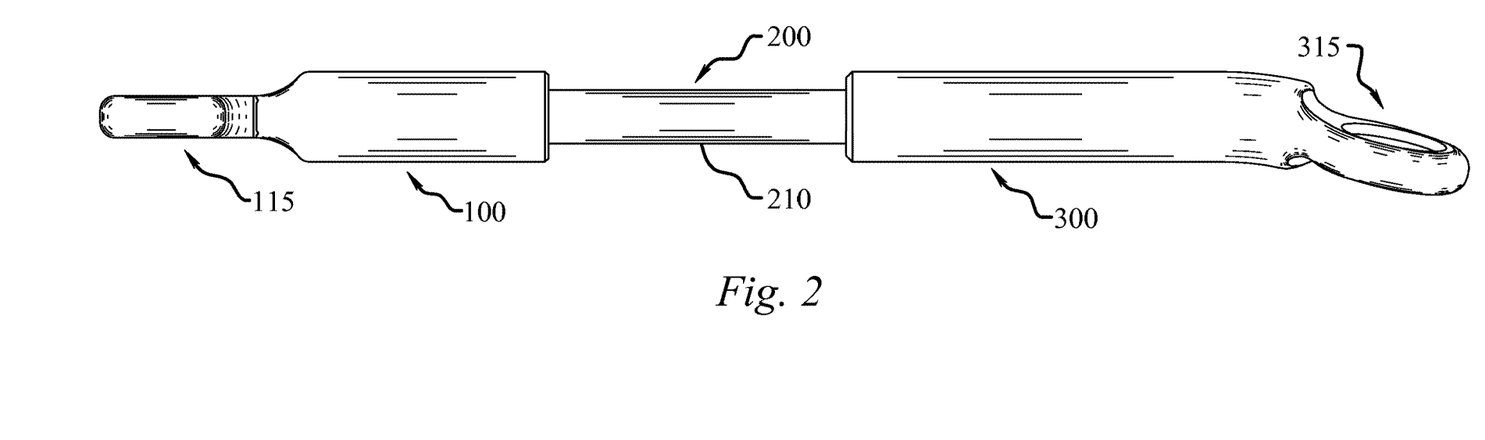
FIG. 2 is a top perspective view of the dental orthotic strut of FIG. 1.
Figure 3:
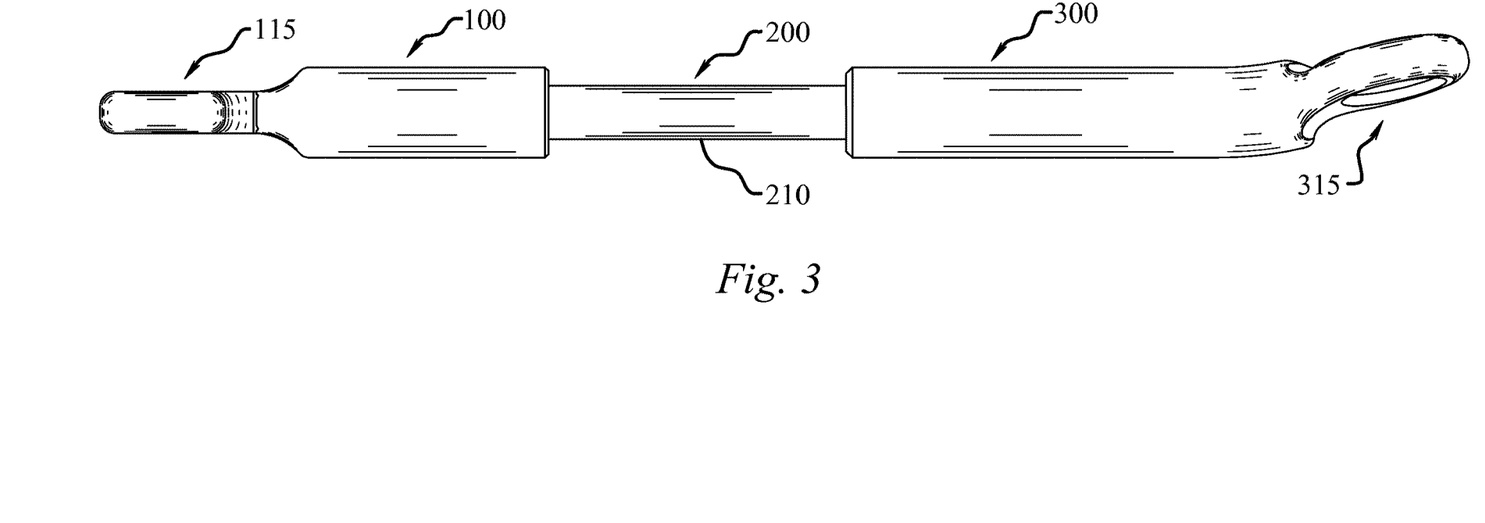
FIG. 3 is a top perspective view of another dental orthotic strut, having an opposite anterior barrel anchor angulation to that shown in FIGS. 1 and 2.
Figure 4:
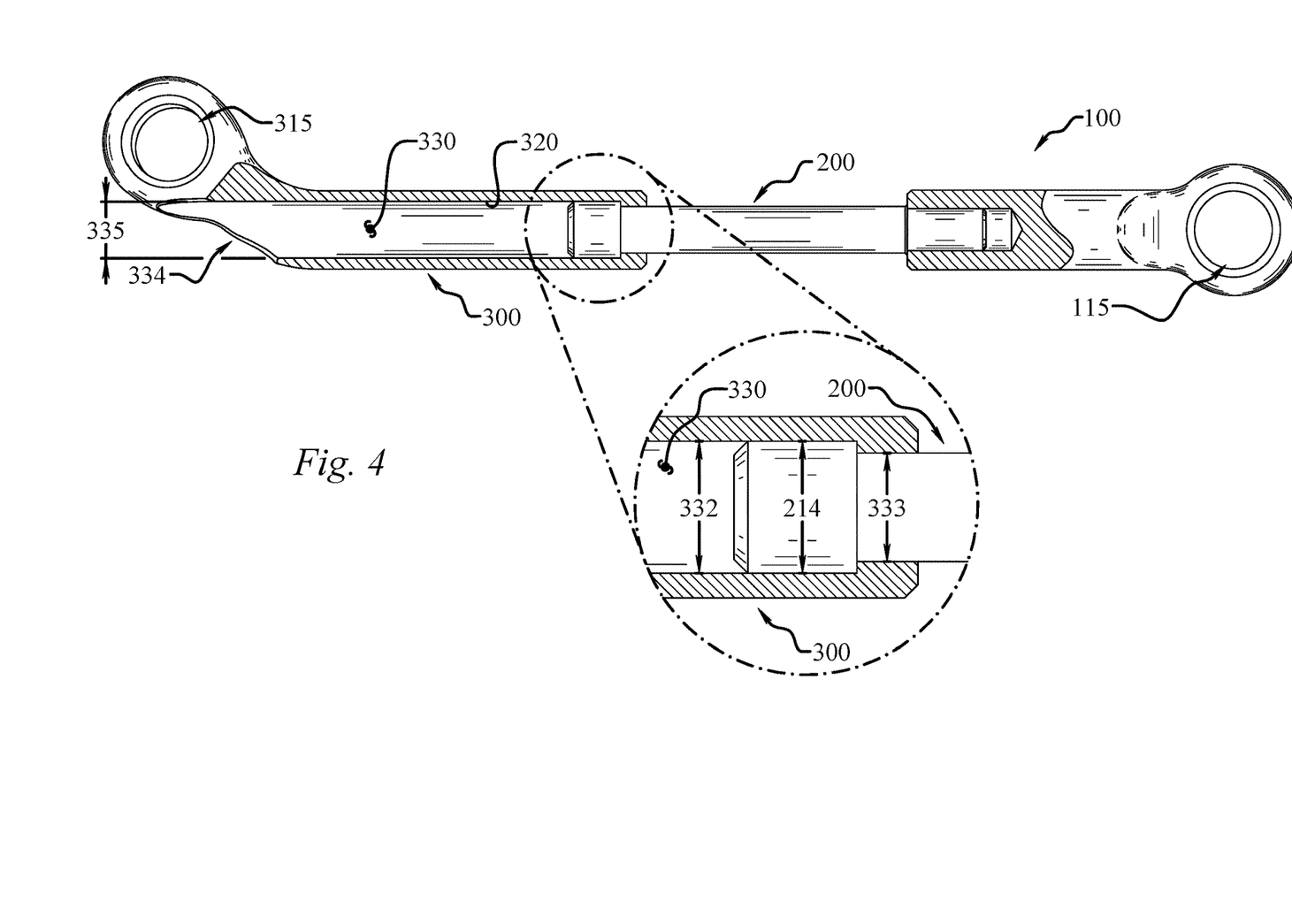
FIG. 4 is a side cross-section view of the dental orthotic strut of FIG. 1, with enlarged areas provided for clarity.
Figure 6:
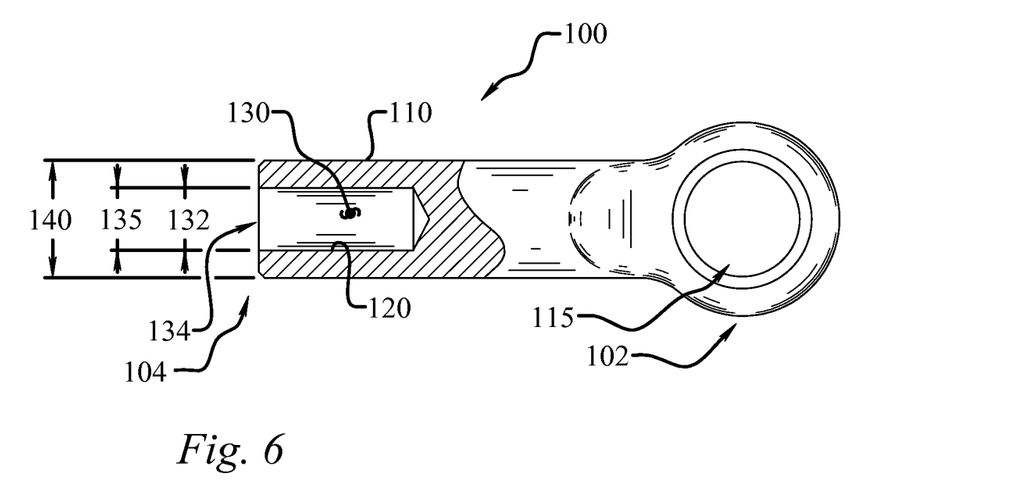
FIG. 6 is side cross-section view of another portion of the dental orthotic strut of FIG. 1.
Figure 7:
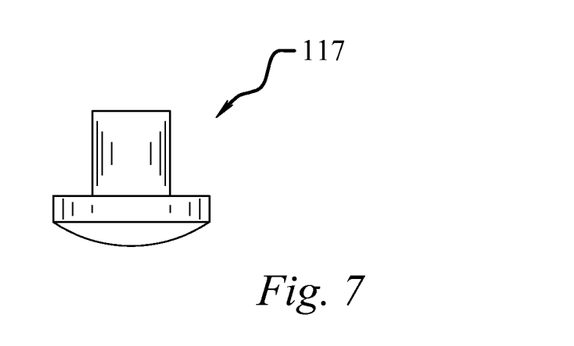
FIG. 7 is a side plan view of a portion of a dental orthotic strut.
Figure 8:
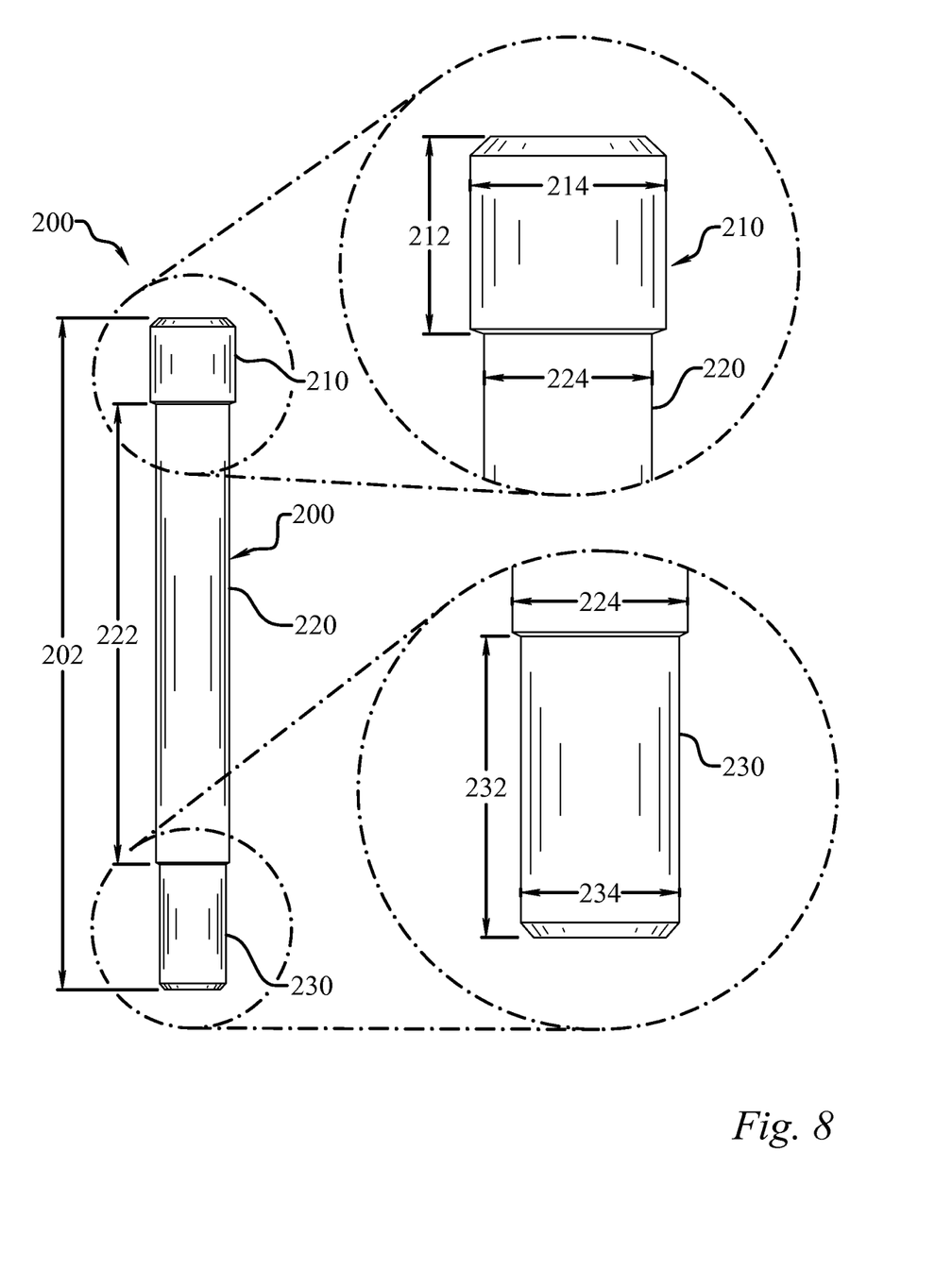
FIG. 8 is a side plan view of a portion of the dental orthotic strut of FIG. 1, with enlarged areas provided for clarity.

In one embodiment, seen well in FIGS. 4 and 6, the posterior barrel (100) may have a posterior barrel lumen (130) within the posterior barrel (100), having a posterior barrel lumen interior surface (120), a posterior barrel lumen diameter (132), and a posterior barrel lumen forward fenestration (134) with a posterior lumen forward fenestration diameter (135). In such an embodiment, the piston stem portion (230) may pass through the posterior barrel lumen forward fenestration (134) and into the posterior barrel lumen (130), where it may be fixed within the posterior barrel forward end (104), as seen well in FIG. 4. Such an inset construction may simplify the joining of the piston stem portion (230) to the posterior barrel (100), as well as contribute to a stronger joining.

One skilled in the art will see that although the present disclosure details a strut (10) having a piston with a fixed posterior joining and an rotable anterior joining, an orthotic could well be built using a "mirror" construction, that is, a rotable posterior joining and a fixed anterior joining. Equally well, an orthotic could be made have both an anterior and a posterior rotable joint; and these embodiments are all considered within the intent of the present disclosure.

Figure 9:
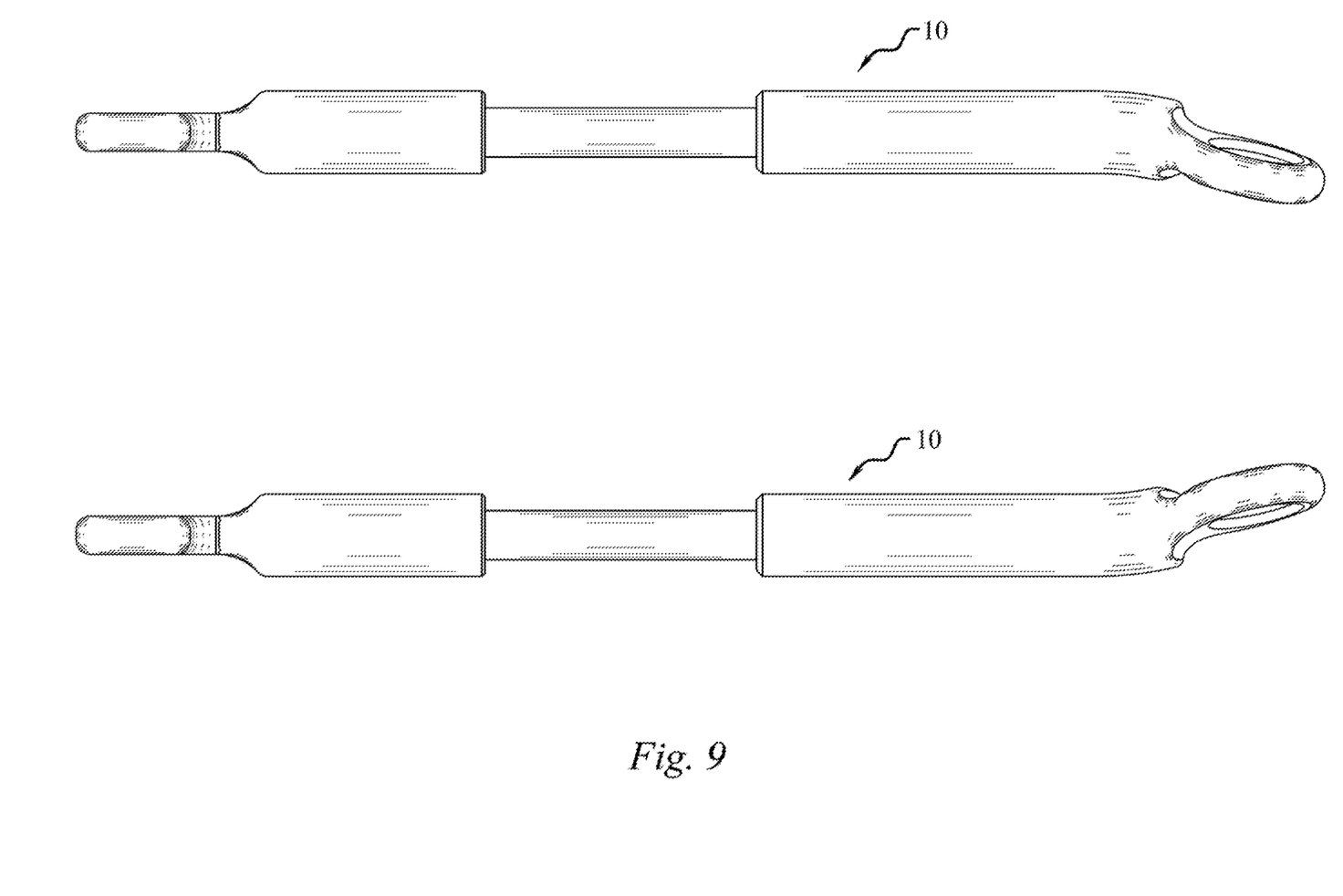
FIG. 9 is a top perspective view of a pair of struts according to an embodiment of the instant invention, having a left strut and a right strut.
Figure 10:
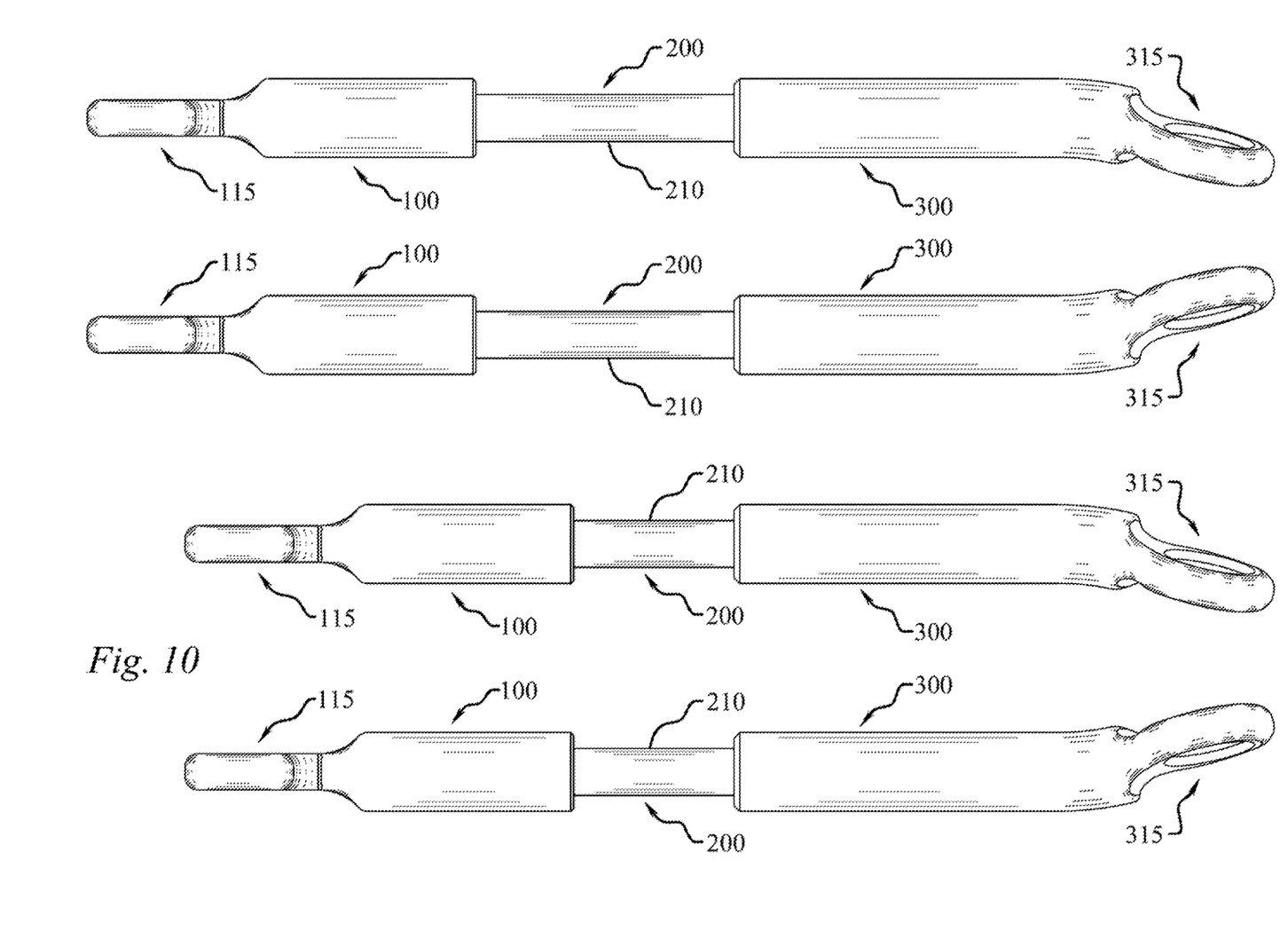
FIG. 10 is a top perspective view of two pairs of struts according to an embodiment of the instant invention, each pair having a left strut and a right strut of the same length, and the two pairs of struts having different overall length between them.

In a preferred embodiment, an orthotic may include a pair of struts (10) comprising a left strut (10) and a right strut (10) having a same length, seen well in FIG. 9. An orthotic may be supplied or configured with a plurality of pairs of struts (10), as seen well in FIG. 10, with each pair having a same length between the pair members, but having a different length from the remaining pairs of struts (10). As would be seen by one skilled in the art, such a plurality of pairs of struts (10) with each pair having a different length, may facilitate progressive lower-jaw advancement.

Figure 5:
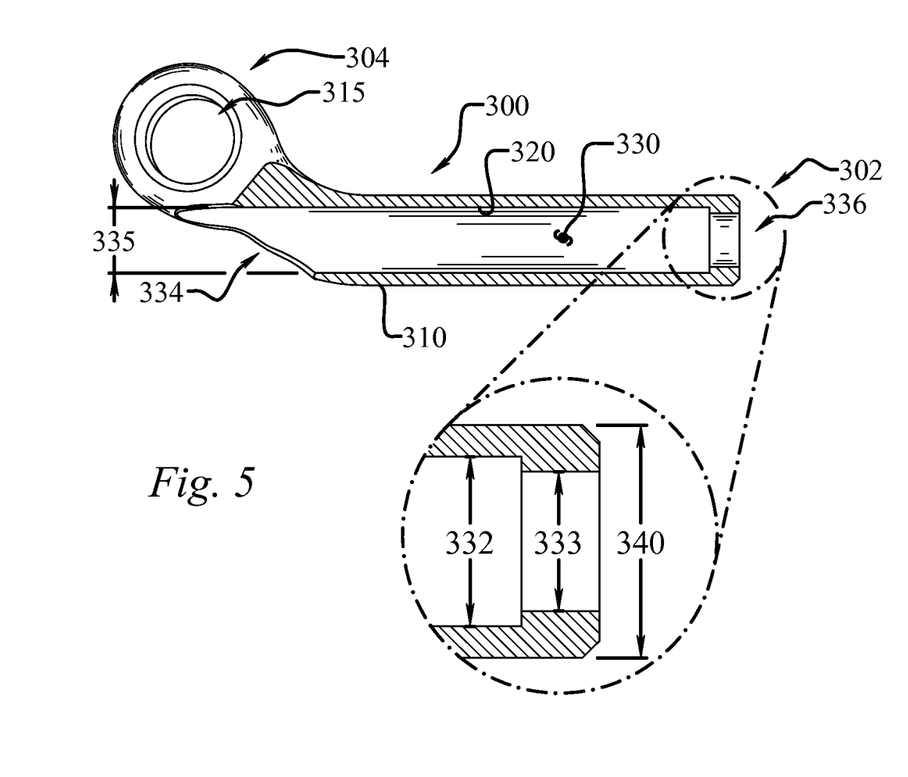
FIG. 5 is side cross-section view of a portion of the dental orthotic strut of FIG. 1, with enlarged areas provided for clarity.

In a preferred embodiment, seen well in FIGS. 4 and 5, the anterior barrel lumen (330) may include an anterior barrel lumen forward fenestration (334) having an anterior barrel lumen forward fenestration diameter (335), wherein the anterior barrel lumen forward fenestration diameter (335) is greater than the piston retainer diameter (214). In such an embodiment, the piston (200) may be inserted in the anterior barrel (300) after the anterior barrel (300) is fully fabricated, by slipping the piston stem end portion (230) and piston working body portion (220) into the anterior barrel lumen (330) and through the anterior barrel rearward fenestration (336).

As seen well in FIG. 4, the piston retainer diameter (214) may be less than the anterior barrel lumen first diameter (332), but greater than the anterior barrel lumen second diameter (333), the piston (200) will not pass through the anterior barrel rearward fenestration (336), even though the anterior barrel lumen (330) may be open to an atmosphere and the piston retainer portion (214) may be less than the anterior barrel lumen first diameter (332). As the piston stem portion (230) is fixed to the posterior barrel forward end (104), and the piston overall length (202) may be less that an anterior barrel lumen length, the piston (200) will not be displaceable from the anterior barrel (300), even if the anterior barrel lumen (330) is fully open at the anterior barrel forward end (304).

Such a construction has even been found to contribute a "self-cleaning" aspect to the invention, in that food or other detritus that may enter the anterior barrel lumen 330) tends to be pushed forward and out of the anterior barrel forward fenestration (334) by a back-and-forth action of the piston (200).

In one preferred embodiment, among others, seen well in FIGS. 1-8, a dental orthotic strut (10), may include a posterior barrel (100) having a posterior barrel rearward end (102) having a posterior barrel anchor (115) rotably attachable to the mandibular portion of a dental orthotic by a removable anchor pin (117), seen well in FIGS. 1, 4, 6, and 7. There may be a posterior barrel forward end (104), a posterior barrel exterior surface (110), a posterior barrel external diameter (140), a posterior barrel lumen (130) within the posterior barrel (100) having a posterior barrel lumen interior surface (120), a posterior barrel lumen diameter (132), and a posterior barrel lumen forward fenestration (134) with a posterior lumen forward fenestration diameter (135). In many embodiments, the posterior barrel lumen diameter (132) may be equal or nearly equal to the posterior lumen forward fenestration diameter (135).

Such an embodiment may include a piston (200), seen well in FIGS. 2, 3, 4, and 8, having a piston overall length (202), a piston retainer portion (210) having a piston retainer length (212) and a piston retainer diameter (214); a piston working body portion (220) having a piston working body length (222) and a piston working body diameter (224), and a piston stem portion (230) having a piston stem length (232) and a piston stem diameter (234). An anterior barrel (300), seen well in FIGS. 1, 4, and 5, may have an anterior barrel rearward end (302) and an anterior barrel forward end (304) having an anterior barrel lumen forward fenestration (334) with an anterior lumen forward fenestration diameter (335) greater than the piston retainer diameter (214). An anterior barrel anchor (315) may be rotably attachable to a maxillary portion of the dental orthotic by a removable anchor pin (117). The anterior barrel may have an anterior barrel exterior surface (310), an anterior barrel internal surface (320), an anterior barrel first external diameter (340), an anterior barrel lumen (330) within the anterior barrel (300) having an anterior barrel lumen interior surface (320), an anterior barrel lumen first diameter (332), an anterior barrel lumen second diameter (333), and an anterior barrel rearward fenestration (336).

As seen well in FIG. 4, the piston stem portion (230) and the piston working body portion (220) may pass through the anterior barrel rearward fenestration (336), the piston retainer diameter (214) being greater than the anterior barrel lumen second diameter (333) and less than the anterior barrel lumen first diameter (332), thereby movably retaining the piston (200) within the anterior barrel lumen (330) and preventing the overall length of the piston (202) from fully passing through the anterior barrel rearward fenestration (336). As seen well in FIG. 4, the piston stem portion (230) may pass through the posterior barrel lumen forward fenestration (134) into the posterior barrel lumen (130) and be fixed within the posterior barrel lumen (130).

In some embodiments, the posterior barrel external diameter (140) is approximately equal to the anterior barrel external diameter (340), but this is not required. In other embodiments, the anterior barrel anchor (315) is angulated at about a ten degree angle from a longitudinal axis of the anterior barrel (300). In yet other embodiments, the piston stem portion (230) is permanently affixed to the posterior barrel (100) in a rigid joint, and rigid joint may include a welded joint, an adhered joint, and/or a press-fit joint.

In some preferred embodiments, the strut (10) may be supplied or configured as a plurality of pairs of struts (10)

having a same length, with each pair of struts (10) having a different length from the remaining pairs of struts (10). In such embodiments, a posterior barrel length of between 7.5 millimeters and 12.5 millimeters, measured along a longitudinal axis of the posterior barrel (100) from a center of the posterior barrel anchor (115) to the posterior barrel forward end (104), has been found to work well.

In yet other embodiments, a strut (10) may be made, at least in part, or a resilient material that may provide expansive force when deformed from an at rest state, as well as being provided with one or more joints. By way of example and not limitation only, at least one strut element such as the posterior barrel (100), the piston (200) and/or the anterior barrel (300) may include a resilient material having at least a first at-rest length. In an operating position, a straight-line distance between the ratable attachment of the mandibular portion of the dental orthotic to the posterior barrel anchor (115) and the rotable attachment of the maxillary portion of the dental orthotic to the anterior barrel anchor (315) may be less than the at least first at-rest length. Such a construction is entirely compatible with one or more multi-axis rotable joints as previously described.

Many of the embodiments of the dental orthotic strut (10) are useful in a method of effecting the progressive advancement of a lower jaw. Such a method would include, but not necessarily be limited to, the following steps:

A baseline step would be the providing of a dental orthotic having a maxillary portion capable of reversibly attaching to a plurality of maxillary teeth of a patient and a mandibular portion capable of reversibly attaching to a plurality of mandibular teeth of a patient. Next, one would reversibly and rotably attach the maxillary portion to the mandibular portion with at least a first strut (10).

Such a strut (10) may have a posterior barrel (100), seen well in FIGS. 1, 2, 3, 4 and 6, having a posterior barrel rearward end (102) having a posterior barrel anchor (115) rotably attachable to the mandibular portion, a posterior barrel forward end (104), a posterior barrel exterior surface (110); and a posterior barrel external diameter (140). Such a posterior barrel 5 (100) may further have a predetermined first overall length measured along a longitudinal axis of the posterior barrel (100) from a center of the posterior barrel anchor (115) to the posterior barrel forward end (104).

The strut (10) may include a piston (200), seen well in FIGS. 1, 2, 4 and 8, having a piston overall length (202), a piston retainer portion (210) having a piston retainer length (212) and a piston retainer diameter (214); a piston working body portion (220) having a piston working body length (222); and a piston working body diameter (224), a piston stem portion (230) having a piston stem length (232) and a piston stem diameter (234).

The strut may have an anterior barrel (300), seen well in FIGS. 1-5, having an anterior barrel rearward end (302) and an anterior barrel forward end (304) having an anterior barrel anchor (315) ratably attachable to the maxillary portion, an anterior barrel exterior surface (310), an anterior barrel external surface (310), an anterior barrel internal surface (320), an anterior barrel first external diameter (340), an anterior barrel lumen (330) within the anterior barrel (300) having an anterior barrel lumen interior surface (320), an anterior barrel lumen first diameter (332), an anterior barrel lumen second diameter (333), and an anterior barrel rearward fenestration (336).

In such a strut (10), seen well in FIG. 4, the piston stem portion (230) and the piston working body portion (220) may pass through the anterior barrel rearward fenestration (336) the piston retainer diameter (214) being greater than the anterior barrel lumen second diameter 33) and less than the anterior barrel lumen first diameter (332), thereby movably retaining the piston (200) within the anterior barrel lumen (330) and preventing the overall length of the piston (202) from fully passing through the anterior barrel rearward fenestration (336). The piston stein portion (230) may be fixed to the posterior barrel forward end (104).

A following step would include releasably attaching the maxillary portion to the plurality of maxillary teeth of a patient and the mandibular portion to the plurality of mandibular teeth of a patient, thereby displacing a lower jaw in a forward direction. While a preferred embodiment allows a patient to place and remove the maxillary and mandibular portions from the teeth, in an alternative method, the maxillary and mandibular portions may require professional attachment and removal from the teeth, as would be known to one familiar with the traditional Herbst appliance.

A length of time would be observed, during which one might periodically remove the orthotic and measure a degree of the displacement of the lower jaw. During a period while the orthotic is removed from the patient, one may remove the first strut (10) from the maxillary and mandibular portion and replace it with a similar strut (10) having a second, and greater, predetermined length. Frequently, the strut (10) is supplied as a plurality of pairs of left and right struts (10), with each left and right strut having a same length between any two pair members, but having a different strut length among the plurality of pairs of struts (10).

The above steps would then be repeated, with a slightly longer strut (10) being employed with each cycle of the method, until a predetermined degree of lower jaw advancement has been obtained. Treatment would conclude by removing the orthotic from the teeth of the patient. The method could include the step of the step of measuring at least one blood oxygen saturation of the patient during the performance of at least one of the steps. A pulse oximeter is ideal for such measurements, although invasive methods well-known in the art could also be employed.

Numerous alterations, modifications, and variations of the preferred embodiments disclosed herein will be apparent to those skilled in the art and they are all anticipated and contemplated to be within the spirit and scope of the disclosed dental orthotic strut (10). For example, although specific embodiments have been described in detail, those with skill in the art will understand that the preceding embodiments and variations can be modified to incorporate various types of substitute and or additional or alternative materials, relative arrangement of elements, and dimensional configurations. Accordingly, even though only few variations of the dental orthotic strut (10) are described herein, it is to be understood that the practice of such additional modifications and variations and the equivalents thereof, are within the spirit and scope of the dental orthotic strut (10) as disclosed herein. The corresponding structures, materials, acts, and equivalents of all means or step plus function elements in the claims below are intended to include any structure, material, or acts for performing the functions in combination with other claimed elements as specifically claimed.

I claim:
1. A dental orthotic strut (10), comprising:
a posterior barrel (100) having a posterior barrel rearward end (102) having a posterior barrel anchor (115), a posterior barrel forward end (104), a posterior barrel exterior surface (110), and a posterior barrel external diameter (140);

a piston (200) having a piston overall length (202), a piston retainer portion (210) having a piston retainer length (212) and a piston retainer diameter (214), a piston working body portion (220) having a piston working body length (222) and a piston working body diameter (224), a piston stem portion (230) having a piston stem length (232) and a piston stem diameter (234);

an anterior barrel (300) having an anterior barrel rearward end (302) and an anterior surface (310), an anterior barrel external diameter (340), an anterior barrel lumen (330) within the anterior barrel (300) having an anterior barrel lumen interior surface (320), an anterior barrel lumen first diameter (332), an anterior barrel lumen second diameter (333), and an anterior barrel rearward fenestration (336) wherein the anterior barrel lumen (330) further comprises an anterior barrel lumen forward fenestration (334) having an anterior barrel lumen forward fenestration diameter (335), wherein the anterior barrel lumen forward fenestration diameter (335) is greater than the piston retainer diameter (214);

wherein the piston stem portion (230) passes through the anterior barrel rearward fenestration (336), the piston retainer diameter (214) being greater than the anterior barrel lumen second diameter (333) and less than the anterior barrel lumen first diameter (332), thereby movably retaining the piston (200) within the anterior barrel lumen (330), allowing free movement of the piston working body length (222) in an axial direction through a full range of motion of the piston working body length (222) within the anterior barrel lumen (330) and, and allowing particulate matter to be expelled from the anterior barrel lumen (330) through the anterior barrel lumen forward fenestration (334), while preventing the overall length of the piston (202) from fully passing through the anterior barrel rearward fenestration (336); and the piston stem portion (230) is fixed to the posterior barrel forward end (104).

2. The device according to claim 1, wherein the posterior barrel (100) has a posterior barrel lumen (130) within the posterior barrel (100) having a posterior barrel lumen interior surface (120), a posterior barrel lumen diameter (132), and a posterior barrel lumen forward fenestration (134) having a posterior lumen forward fenestration diameter (135); and the piston stem portion (230) passes through the posterior barrel lumen forward fenestration (134) into the posterior barrel lumen (130) and is fixed within the posterior barrel forward end (104).

3. The device according to claim 1, further comprising a pair of dental orthotic struts (10) comprising pair members consisting of a left strut (10) and a right strut (10) having a same length.

4. The device according to claim 3, wherein the strut (10) further comprises a plurality of pairs of struts (10), wherein each pair off struts (10) further comprises pair members consisting of a left strut (10) and a right strut (10) having a same length, with each pair member having a different length from the remaining pairs of struts (10).

5. The device according to claim 1, wherein a removable anchor pin (117) rotably attaches the posterior barrel anchor (115) to a mandibular portion of a dental orthotic and a removable anchor pin (117) rotably attaches the anterior barrel anchor (315) to the maxillary portion of the dental orthotic.

6. The device according to claim 5, wherein at least one strut element selected from the group of elements consisting of the posterior barrel (100), the piston (200) and the anterior barrel (300) further comprises a resilient material having at least a first at-rest length and wherein in an operating position, a straight-line distance between the rotable attachment of the mandibular portion of the dental orthotic to the posterior barrel anchor (115) and the rotable attachment of the maxillary portion of the dental orthotic to the anterior barrel anchor (315) is less than the at least first at-rest length.

7. The device according to claim 1, wherein the anterior barrel anchor (315) is angulated at about a ten degree angle from a longitudinal axis of the anterior barrel (300).

8. The device according to claim 1, wherein the piston stem portion (230) is affixed to the posterior barrel (100) in a rigid joint.

9. The device according to claim 8, wherein the rigid joint is selected from the group of rigid joints consisting of a welded joint, an adhered joint, and a press-fit joint.

10. The device according to claim 1, wherein the posterior barrel (100), measured along a longitudinal axis of the posterior barrel (100) from a center of the posterior barrel anchor (115) to the posterior barrel forward end (104), has an overall length of between 7.5 millimeters and 12.5 millimeters.

11. A dental orthotic strut (10), comprising:

a posterior barrel (100) having a posterior barrel rearward end (102) having a posterior barrel anchor (115) rotably attachable to the mandibular portion of a dental orthotic by a removable anchor pin (117), a posterior barrel forward end (104), a posterior barrel exterior surface (110), a posterior barrel external diameter (140), a posterior barrel lumen (130) within the posterior barrel (100) having a posterior barrel lumen interior surface (120), a posterior barrel lumen diameter (132), and a posterior barrel lumen forward fenestration (134) having a posterior barrel lumen forward fenestration diameter (135);

a piston (200) having a piston overall length (202), a piston retainer portion (210) having a piston retainer length (212) and a piston retainer diameter (214), a piston working body portion (220) having a piston working body length (222) and a piston working body diameter (224), a piston stem portion (230) having a piston stem length (232) and a piston stem diameter (234);

an anterior barrel (300) having an anterior barrel rearward end (302) and an anterior barrel forward end (304) having an anterior barrel lumen forward fenestration (334) with an anterior lumen forward fenestration diameter (335), greater than the piston retainer diameter (214), an anterior barrel anchor (315) rotably attachable to a maxillary portion of the dental orthotic by a removable anchor pin (117), an anterior barrel exterior surface (310), an anterior barrel first external diameter (340), an anterior barrel lumen (330) within the anterior barrel (300) having an anterior barrel lumen interior surface (320), an anterior barrel lumen first diameter (332), an anterior barrel lumen second diameter (333), and an anterior barrel rearward fenestration (336);

wherein the piston stem portion (230) passes through the anterior barrel rearward fenestration (336), the piston retainer diameter (214) being greater than the anterior barrel lumen second diameter (333) and less than the anterior barrel lumen first diameter (332), thereby movably retaining the piston (200) within the anterior barrel lumen (330), allowing free movement of the piston working body length (222) in an axial direction through a full range of motion of the piston working body length (222) within the anterior barrel lumen (330) and, and allowing particulate matter to be expelled from the anterior barrel lumen (330) through the anterior barrel lumen forward fenestration (334), while preventing the overall length of the piston (202) from fully passing through the anterior barrel rearward fenestration (336); and the piston stem portion (230) passes through the posterior barrel lumen forward fenestration (134) into the posterior barrel lumen (130) and is fixed within the posterior barrel lumen (130).

12. The device according to claim 11, wherein the strut (10) further comprises a plurality of pairs of struts (10), wherein each pair of struts (10) further comprises pair members consisting of a left strut (10) and a right strut (10) having a same length, with each pair member having a different length from the remaining pairs of struts (10).

13. The device according to claim 11, wherein the posterior barrel external diameter (140) is approximately equal to the anterior barrel external diameter (340).

14. The device according to claim 11, wherein the anterior barrel anchor (315) is angulated at about a ten degree angle from a longitudinal axis of the anterior barrel (300).

15. The device according to claim 11, wherein the piston stem portion (230) is permanently affixed to the posterior barrel (100) in a rigid joint.

16. The device according to claim 15, wherein the rigid joint is selected from the group of rigid joints consisting of a welded joint, an adhered joint, and a press-fit joint.

17. The device according to claim 11, wherein the posterior barrel (100), measured along a longitudinal axis of the posterior barrel (100) from a center of the posterior barrel anchor (115) to the posterior barrel forward end (104), has an overall length of between 7.5 millimeters and 12.5 millimeters.

* * * * *